United States Patent
Schneider et al.

(10) Patent No.: US 9,320,565 B2
(45) Date of Patent: Apr. 26, 2016

(54) ABLATION DEVICES, SYSTEMS AND METHOD FOR MEASURING COOLING EFFECT OF FLUID FLOW

(75) Inventors: Clinton W. Schneider, Plymouth, MN (US); John P. Gerhart, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1984 days.

(21) Appl. No.: 12/347,558

(22) Filed: Dec. 31, 2008

(65) Prior Publication Data
US 2010/0168738 A1    Jul. 1, 2010

(51) Int. Cl.
*A61B 18/14*    (2006.01)
*A61B 18/12*    (2006.01)
(Continued)

(52) U.S. Cl.
CPC ......... *A61B 18/1492* (2013.01); *A61B 18/1206* (2013.01); *A61B 2018/00011* (2013.01); *A61B 2018/00642* (2013.01); *A61B 2018/00648* (2013.01); *A61B 2018/00702* (2013.01);
(Continued)

(58) Field of Classification Search
CPC ........... A61B 18/1206; A61B 18/1492; A61B 2018/00648; A61B 2018/00702; A61B 2018/00642; A61B 2018/00791; A61B 2018/00011; A61M 2019/464
See application file for complete search history.

(56) References Cited

U.S. PATENT DOCUMENTS

| | | | |
|---|---|---|---|
| 5,346,508 A | * | 9/1994 | Hastings ................ A61B 5/028 600/505 |
| 5,348,554 A | | 9/1994 | Imran et al. |
| 5,423,811 A | | 6/1995 | Imran et al. |

(Continued)

FOREIGN PATENT DOCUMENTS

WO    2007067628    6/2007

OTHER PUBLICATIONS

Ebefors et al, "Three Dimensional Silicon Triple-Hot-Wire Anemometer Based on Polyimide Joints", MEMS, 1998. MEMS 98. Proceedings., The Eleventh Annual International Workshop on, pp. 93-98.*

(Continued)

*Primary Examiner* — Andrew Gilbert
(74) *Attorney, Agent, or Firm* — Wiley Rein LLP

(57) ABSTRACT

Disclosed herein are various catheter and catheter systems that are useful in ablating tissue that is also subject to surface perfusion, for example blood flow across and/or through tissue. A representative embodiment of a catheter useful with the present invention includes an anemometer located on an exterior surface of the distal portion of the catheter. The anemometer is thermally isolated from the distal tip to permit the anemometer to measure the cooling effect of surface perfusion. The ablation catheter may include thermal insulation to insulate the anemometer from the distal tip. Alternatively, and/or in addition, the anemometer may be positioned proximally of the distal tip. The catheter may include one or more temperature sensors thermally coupled to the distal tip to measure the temperature of the distal tip. The distal tip may include one or more spiral grooves, or one or more holes. It is contemplated that the anemometer may be positioned within any such spiral groove or hole using a thermal insulation material, such as a non-conductive adhesive. The catheter may optionally include a contact sensor on the distal portion to assess a degree of contact between the ablation catheter and tissue being treated. Various ablation systems and methods are described herein that utilize catheters as described above.

27 Claims, 4 Drawing Sheets

(51) Int. Cl.
*A61B 18/00* (2006.01)
*A61B 19/00* (2006.01)

(52) U.S. Cl.
CPC . *A61B2018/00791* (2013.01); *A61B 2019/464* (2013.01)

(56) References Cited

U.S. PATENT DOCUMENTS

| | | | |
|---|---|---|---|
| 5,427,119 | A | 6/1995 | Swartz et al. |
| 5,431,649 | A | 7/1995 | Mulier et al. |
| 5,433,708 | A | 7/1995 | Nichols et al. |
| 5,497,774 | A | 3/1996 | Swartz et al. |
| 5,545,161 | A | 8/1996 | Imran |
| 5,697,927 | A | 12/1997 | Imran et al. |
| 5,779,669 | A | 7/1998 | Haissaguerre et al. |
| 5,779,699 | A | 7/1998 | Lipson |
| 5,782,828 | A | 7/1998 | Chen et al. |
| 5,785,706 | A | 7/1998 | Bednarek |
| 5,792,140 | A | 8/1998 | Tu et al. |
| 5,807,395 | A | 9/1998 | Mulier et al. |
| 5,843,020 | A | 12/1998 | Tu et al. |
| 5,843,152 | A | 12/1998 | Tu et al. |
| 5,849,028 | A | 12/1998 | Chen |
| 5,876,399 | A | 3/1999 | Chia et al. |
| 5,913,856 | A | 6/1999 | Chia et al. |
| 5,916,213 | A | 6/1999 | Haissaguerre et al. |
| 5,921,924 | A | 7/1999 | Avitall |
| 5,954,665 | A | 9/1999 | Ben-Haim |
| 5,971,983 | A | 10/1999 | Lesh |
| 5,980,516 | A | 11/1999 | Mulier et al. |
| 6,016,809 | A | 1/2000 | Mulier et al. |
| 6,033,403 | A | 3/2000 | Tu et al. |
| 6,068,629 | A | 5/2000 | Haissaguerre et al. |
| 6,120,500 | A | 9/2000 | Bednarek et al. |
| 6,132,426 | A | 10/2000 | Kroll |
| 6,138,043 | A | 10/2000 | Avitall |
| 6,214,002 | B1 | 4/2001 | Fleischman et al. |
| 6,235,022 | B1 | 5/2001 | Hallock et al. |
| 6,235,025 | B1 | 5/2001 | Swartz et al. |
| 6,308,091 | B1 | 10/2001 | Avitall |
| 6,387,052 | B1 * | 5/2002 | Quinn et al. ............ 600/505 |
| 6,403,426 | B1 | 6/2002 | Montree et al. |
| 6,436,087 | B1 * | 8/2002 | Lewis et al. ............ 604/508 |
| 6,447,507 | B1 | 9/2002 | Bednarek et al. |
| 6,485,430 | B1 * | 11/2002 | Quinn et al. ............ 600/505 |
| 6,544,262 | B2 | 4/2003 | Fleischman |
| 6,663,622 | B1 | 12/2003 | Foley et al. |
| 6,666,862 | B2 * | 12/2003 | Jain et al. ............ 606/41 |
| 6,689,128 | B2 | 2/2004 | Sliwa, Jr. et al. |
| 6,701,931 | B2 | 3/2004 | Sliwa, Jr. et al. |
| 6,702,811 | B2 | 3/2004 | Stewart et al. |
| 6,858,026 | B2 | 2/2005 | Sliwa, Jr. et al. |
| 6,923,806 | B2 | 8/2005 | Hooven et al. |
| 6,955,675 | B2 * | 10/2005 | Jain ............ 606/41 |
| 6,971,274 | B2 * | 12/2005 | Olin ............ 73/866.5 |
| 7,013,725 | B1 * | 3/2006 | Hagan et al. ............ 73/204.15 |
| 7,072,776 | B2 * | 7/2006 | Hagan et al. ............ 702/47 |
| 7,282,049 | B2 | 10/2007 | Orszulak et al. |
| 7,321,833 | B2 * | 1/2008 | DuHack et al. ............ 702/47 |
| 7,333,899 | B2 * | 2/2008 | Zimmermann et al. ....... 702/45 |
| 8,221,409 | B2 * | 7/2012 | Cao et al. ............ 606/41 |
| 8,641,705 | B2 * | 2/2014 | Leo et al. ............ 606/34 |
| 8,702,688 | B2 * | 4/2014 | Melsky ............ 606/14 |
| 8,906,011 | B2 * | 12/2014 | Gelbart et al. ............ 606/41 |
| 2002/0068866 | A1 * | 6/2002 | Zikorus et al. ............ 600/424 |
| 2002/0123749 | A1 * | 9/2002 | Jain ............ 606/41 |
| 2002/0169445 | A1 * | 11/2002 | Jain et al. ............ 606/41 |
| 2003/0236487 | A1 | 12/2003 | Knowlton |
| 2005/0222554 | A1 | 10/2005 | Wallace et al. |
| 2006/0095022 | A1 | 5/2006 | Moll et al. |
| 2006/0100610 | A1 | 5/2006 | Wallace et al. |
| 2007/0049915 | A1 | 3/2007 | Haemmerich et al. |
| 2009/0131930 | A1 * | 5/2009 | Gelbart ............ A61B 18/1492 606/41 |
| 2010/0168738 | A1 * | 7/2010 | Schneider et al. ............ 606/41 |

OTHER PUBLICATIONS

International Search Report for International Application No. PCT/US08/083828 filed Nov. 17, 2008, dated Jan. 22, 2009.
Medtronic, RF Generators, ATAKR II Advanced RF Ablation System, Metronic, Inc. 2007.
Medcompare, Atakr II RF Ablation System, Medcompare.com, 2003-2008.
Medtronic, Atakr II Advanced RF Ablation System, Medtronic, Inc. 2000.
Medtronic, Inc., Radio Frequency Catheter Ablation Generator, ATAKR II, Uchisearch, LLC 2007-2008.
Citarella, J., Peltier Basics, Jan. 17, 2000.
Webster, J. G., The Measurement Instrumentation and Sensors Handbook, Point Velocity Measurement, No. 29 pp. 16-37, 1999.
Cooper, J. M., et al., A Rewarming Maneuver Demonstrates the Contribution of Blood Flow to Electrode Cooling During Internally Irrigated RF Ablation, Journal of Cardiovascular Electrophysiology, vol. 19, No. 4, pp. 409-414, Apr. 4, 2008.

* cited by examiner

ABLATION DEVICES, SYSTEMS AND METHOD FOR MEASURING COOLING EFFECT OF FLUID FLOW

BACKGROUND OF THE INVENTION a. Field of the Invention

The present invention relates generally to an ablation catheter and method for using ablation catheters. In particular, the present invention relates to methods and devices for measuring tissue cooling and for estimating lesion characteristics as the lesion is being formed.

b. Background Art

Catheters are used for an ever growing number of medical procedures. To name just a few examples, catheters are used for diagnostic, therapeutic, and ablation procedures. Typically, the user manually manipulates the catheter through the patient's vasculature to the intended site, such as a site within the patient's heart. The catheter typically carries one or more electrodes or other diagnostic or therapeutic devices, which may be used for ablation, diagnosis, cardiac mapping, or the like.

It is well known to utilize catheters for ablation treatments. For example, catheters may be used to accomplish ablation by transmission of ablative energy to a desired target area through an electrode assembly to ablate tissue at the target site. Ablative energy may generate significant heat, which if not controlled, can result in excessive tissue damage, such as steam pop, tissue charring, and the like. Accordingly, a need exists to control the delivery of ablation energy and to prevent undesired tissue damage.

Surgical devices and techniques utilizing electrodes to transfer therapeutic energy to tissue are well known. Electrosurgery allows for the incision, cauterization, fulguration, and desiccation of tissue through the application of high-power, radio frequency (RF) energy to tissue through an electrode. Ablation techniques, whereby the target tissue is necrotized through coagulation, are also performed using surgical devices with electrodes to transfer RF energy to tissue. Many benefits may be gained by forming lesions in tissue—for example, control of cardiac arrhythmia or tachycardia, removal of skin diseases, or the treatment of varicose veins—if the depth and location of the lesions being formed can be controlled. In particular, it can be desirable to elevate tissue temperature to around 50-55° C. until lesions are formed via thermal necrosis, which changes the electrical properties of the tissue. For example, when sufficiently deep lesions are formed at specific locations in cardiac tissue via coagulation necrosis, undesirable ventricular tachycardia may be lessened or eliminated. "Sufficiently deep" lesions means transmural lesions in some cardiac applications.

Several difficulties may be encountered, however, when attempting to form adequately-deep lesions at specific locations using some existing surgical ablation electrodes. For example, when forming lesions with ablation energy, high temperature gradients are often encountered in the vicinity of the electrode. At the edges of some existing electrodes are regions of very high current density leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There two types of undesirable coagulum: coagulum that adheres to and damages the medical device; and coagulum blood clots or curds that may enter a patient's bloodstream, possibly resulting in other health problems for the patient. Charring of the surface tissue may also have deleterious effects on a patient.

As the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. Moreover, the use of fluids in the ablation process further complicate the process especially when the application of fluid results in tissue cooling. It is, therefore, a balancing act trying to ensure that tissue temperatures are adequately high for long enough to create deep lesions, while still preventing or minimizing coagulum formation and/or charring of the surface tissue.

Generally, a need exists to control the delivery of ablation energy and to provide greater feedback on tissue temperature, as well as size and other lesion forming characteristics during the ablation process.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

It is desirable to be able to measure the cooling effect caused by blood flowing over tissue during the ablation process. By taking this cooling effect into account, catheters and catheter systems can provide more accurate information regarding the characteristics of lesions being formed.

Disclosed herein in one embodiment is an ablation catheter for ablating tissue that is also subject to surface perfusion, for example blood flow across and/or through tissue. The catheter comprises a proximal portion and a distal portion which in turn has a distal tip. The distal tip has at least one ablation electrode on the tip, and a temperature sensor thermally coupled to the distal tip to measure the temperature of the distal tip. The catheter also includes an anemometer located on an exterior surface of the distal portion. The anemometer is thermally isolated from the distal tip to permit the anemometer to measure the cooling effect of surface perfusion. The ablation catheter may include thermal insulation to insulate the anemometer from the distal tip; alternatively, and/or in addition, the anemometer may be positioned proximally of the distal tip. Optionally, the distal tip may include one or more spiral grooves, or one or more holes. The anemometer may be positioned within a spiral groove or hole using a thermal insulation material, such as a non-conductive adhesive. Preferably, the groove and/or holes are less than about mm wide. The anemometer may comprise a film circuit having a bridge circuit with at least one temperature responsive resistor encased with a thermally-conductive, electrically insulative material, and at least one hot wire located on a surface of the distal portion. Optionally, the catheter may include a contact sensor on the distal portion to assess a degree of contact between the ablation catheter and tissue being treated.

In another embodiment, the present invention comprises an ablation system, having: an ablation catheter as described above; a contact assessment device that assesses a degree of contact between the ablation catheter and tissue being treated; a power source coupled to the catheter to deliver at least one programmable level of power; a clock to measure a time period during which ablative power is delivered to the tissue being treated; a power monitoring device to monitor the amount of ablation power that is delivered by the ablation catheter; and a lesion analysis processor for estimating lesion formation as a function of at least: i) an output of the anemometer that provides information on surface perfusion; ii) an output of the contact assessment device; iii) an output of the clock; and iv) an output of the power monitoring device. The contact assessment device may be a force sensor located on the distal portion of the ablation catheter, or in some embodiments, the contact sensor may be the temperature sensor that is thermally coupled to the distal tip, in which temperature sensor monitors for a change in temperature indicative of contact with the tissue to be treated. Alternatively, the contact assessment device can be the temperature sensor in combination with the ablation electrode and the power source. To assess contact, the system can apply a low level of power sufficient to cause a measurable increase in a temperature of any tissue in contact with the ablation electrode, but insufficient to ablate the tissue, and the temperature sensor can monitor for a change in temperature indicative of tissue being in contact with the ablation electrode. Optionally, the ablation system may include a controller coupled to the power source and to the lesion analysis processor, and the controller can regulate the power source based on information provided by the lesion analysis processor. The system can also include at least one tissue temperature measurement device coupled to the controller such that if the temperature of the tissue being ablated exceeds a maximum desirable temperature, the controller will deactivate the power source. The tissue temperature measurement device can be a thermistor, a thermocouple, or even an anemometer located on an exterior surface of the distal portion such that it can measure a temperature of the tissue being treated. The system may also include an electrophysiology electrode located on the distal portion to measure electrical activity associated with tissue to be treated. The controller is coupled to the electrophysiology electrode and can monitor for a change in an output of the electrophysiology electrode that is indicative of the tissue having been sufficiently ablated to create a conduction block. The controller and/or lesion analysis processor can estimate a size of a lesion as it is being formed during treatment and can deactivate the power source when the estimated lesion size exceeds a target size. The lesion analysis processor can optionally estimate lesion formation as a function of: v) tissue thickness; and vi) internal perfusion.

In another embodiment, the present invention comprises a method of ablating tissue comprising: placing an ablation catheter in contact with tissue to be ablated, activating an ablation energy source to deliver ablation energy to the tissue to be ablated; using an output of the anemometer on the catheter to estimate lesion formation; and deactivating the ablation energy source when an estimated lesion formation reaches a desired level. The catheter preferably has a proximal portion and a distal portion, which distal portion includes a distal tip. The catheter also has an ablation electrode located in the distal tip coupled to the ablation energy source for delivering ablation energy to the tissue. A temperature sensor is thermally coupled to the distal tip to measure the temperature of the distal tip, and an anemometer is located on an exterior surface of the distal portion, and is positioned to permit the anemometer to measure the cooling effect of surface perfusion. The method optionally includes the steps of: assessing a degree of contact between the catheter and tissue being treated; and measuring the amount of ablation energy that is delivered to the tissue being treated as a function of time. These optional steps can be used by a processor to estimate lesion formation as a function of at least: i) an output of the anemometer that indicates an amount of surface perfusion; ii) the assessed degree of contact; and iii) the measured amount of ablation energy that is delivered over a treatment period of time. Optionally, the method includes monitoring a temperature of the tissue being treated and deactivating the ablation energy source if the monitored tissue temperature exceeds a maximum desired tissue temperature. It is also contemplated that the anemometer can be used to estimate the velocity of a fluid passing over the anemometer.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
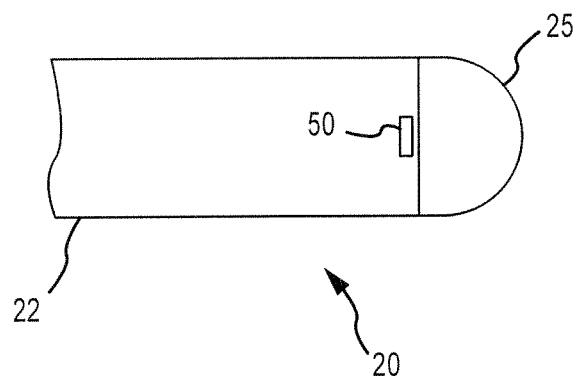
FIG. 1 is a side view of a catheter according to one embodiment of the present invention.

Anemometer circuits are known for measuring flow velocity and/or the pressure associated with the flow. A wide variety of anemometer circuits are appropriate for use with the present invention, including the anemometers disclosed and described in the following patents, all of which are incorporated by reference in their entireties: U.S. Pat. Nos. 7,072,776; 7,321,833; 6,971,274; 7,013,725; and 7,333,899.

A typical anemometer is a hot wire anemometer which uses a very fine wire (perhaps as small as a few micrometers) heated up to some temperature above the ambient. When air or another fluid passes over the wire, it has a cooling effect on the wire. As the electrical resistance of most metals is dependent upon the temperature of the metal (tungsten is a popular choice for hot-wires), a relationship can be obtained between the resistance of the wire and the flow velocity.

There are multiple ways to implement a hot wire anemometer, including without limitation, constant-current anemometers, constant-voltage anemometers, constant-temperature anemometers, and pulse-width-modulated anemometers. The anemometers may be manufactured in a variety of ways, including, film technology. For example, a film could be created using micro-electro mechanical systems ("MEMS"), which will include a bridge circuit layer of resistors, insulated from each other by the film filling material. This film could be punched out and wired into a catheter tip, wrapped around a spiral grove and secured with insulating adhesive, or wrapped around the shaft of the catheter just proximal to the tip, and made flush with the shaft through a selective application of liners over the tubing of the catheter. The temperature sensitive resistors would be comprised of temperature responsive materials, for which conductivity varies based on temperature (platinum or platinum alloy wire, for one example). The film would ideally be a thermally conductive, but electrically insulating material. The rate of change of resistance in the heated wires will indicate the cooling effect of fluid flow over the catheter surface.

One of ordinary skill will appreciate that the output of an anemometer may be readily used to measure the cooling effect of a medium passing over the "hot wire." Typically, the resistance of the "hot wire" may be used to determine the temperature of the medium passing over the "hot wire," but depending upon the anemometer circuit, the cooling effect of the medium passing over the wire may be determined by measuring one or more of the following: voltage, current, resistance and/or temperature. The anemometer may comprise a bridge circuit having at least one hot wire located on a surface of the distal portion and at least one resistor of the bridge circuit located within the catheter.

Aspects of the present invention involve an ablation catheter that has an anemometer circuit positioned to measure the cooling effect of blood and possibly other fluids that may flow over the tissue being ablated. In one particular arrangement, the catheter includes an anemometer circuit that is located proximally of the catheter tip from which the ablation energy is delivered such that its position relative to the thermal effects of the ablation electrode provides a degree of thermal isolation. In other embodiments, the anemometer is located on the catheter tip but is insulated to provide a degree of thermal isolation from the thermal effects of the ablation energy.

The anemometer circuit is ideally positioned in such a way that it effectively measures the cooling effect of blood and other fluids flowing over the tissue to be ablated.

It is desired that the anemometer circuit be thermally isolated from the distal tip. The term "thermally isolated" does not require absolute "thermal isolation" (e.g., the total elimination of heat transfer between the anemometer circuit and the ablation electrode). Rather, the term is used in this specification to mean that the anemometer is sufficiently insulated from the thermal tip such that the convective cooling effect of blood and other fluids flowing across the anemometer has a measurable effect distinguishable from the heating effect of the distal tip; in other words, the anemometer measures the cooling effect of surface perfusion. The insulation may take the form of a material that is non-thermally conductive and/or poorly conductive, or the insulation may take the form of sufficient space to permit the anemometer to effectively measure the cooling effect of the surface perfusion.

In connection with FIG. 1, a catheter according to some embodiments of the present invention will now be described. The catheter 20 generally includes a proximal portion 22 and a catheter tip 25. The catheter tip 25 is typically made of an electrically and thermally conductive material that serves as an ablation electrode. When in use, catheter tip 25 is placed in contact with tissue in need of treatment, and an ablation power source (shown in the block diagram of FIG. 7) provides the ablation energy that is delivered through catheter tip 25 to the tissue. When used intravascularly, blood may flow across the tissue while catheter tip 25 is delivering ablation energy to the tissue. An anemometer 50 is located on the distal portion of the catheter and is disposed such that anemometer 50 can measure the cooling effect of the blood flowing over the tissue being treated (known as "surface perfusion"). In FIG. 1, anemometer 50 is positioned just proximal of the catheter tip 25 so as to more effectively measure the cooling effect of the surface perfusion. The location proximal of the catheter tip 25 permits anemometer to be thermally isolated from the catheter tip 25. As may be discussed below, anemometer 50 may be disposed in other locations on the distal portion of the catheter. Further, any number of anemometer circuits may be utilized as discussed above.

Figure 2:
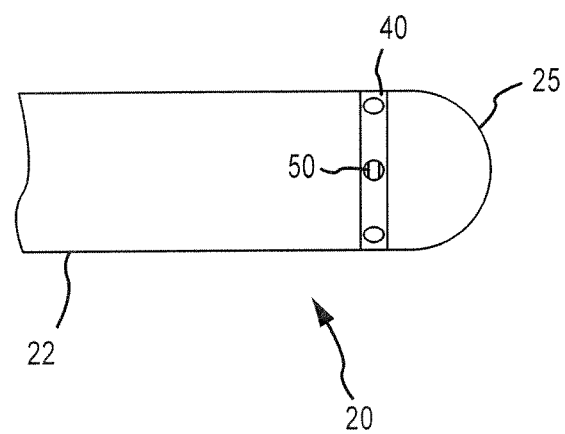
FIG. 2 is a side view of a catheter according to another embodiment of the present invention.

In connection with FIG. 2, a catheter according to other embodiments of the present invention will now be described. The embodiment depicted in FIG. 2 is similar to the embodiment depicted in FIG. 1, and for brevity, the differences will be emphasized with the understanding that the description regarding FIG. 1 above also applies to the embodiment of FIG. 2. The catheter 20 generally includes a proximal portion 22 and a catheter tip 25. A sensor strip 40 is located proximally of the catheter tip 25. The sensor strip 40 may be made of a variety of materials, but preferably, the sensor strip 40 comprises a thermally and electrically non-conductive material. An anemometer 50 is located on an exterior surface of sensor strip 40. For example, sensor strip 40 may include one or more holes, and anemometer 50 may be installed in one of the holes and disposed to be flush with an exterior surface of catheter 20. When catheter 20 is used intravascularly, blood may flow across the tissue while catheter tip 25 is delivering ablation energy to the tissue. An anemometer 50 is disposed such that anemometer 50 can measure the cooling effect of the blood flowing over the tissue being treated. In FIG. 2, anemometer 50 is positioned just proximal of the catheter tip 25 so as to more effectively measure the cooling effect of the surface perfusion. The location proximal of the catheter tip 25 permits anemometer to be thermally isolated from the catheter tip 25. As may be discussed below, anemometer 50 may be disposed in other locations on the distal portion of the catheter. Further, any number of anemometer circuits may be utilized as discussed above. Holes 26 may be formed in the catheter tip 25 in a variety of ways, including for example laser means.

Figure 3:
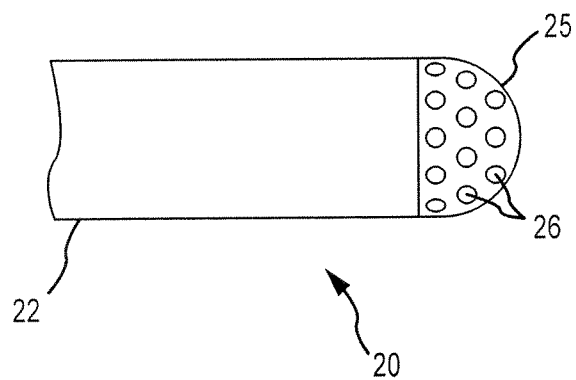
FIG. 3 is a side view of a catheter according to yet another embodiment of the present invention.
Figure 4:
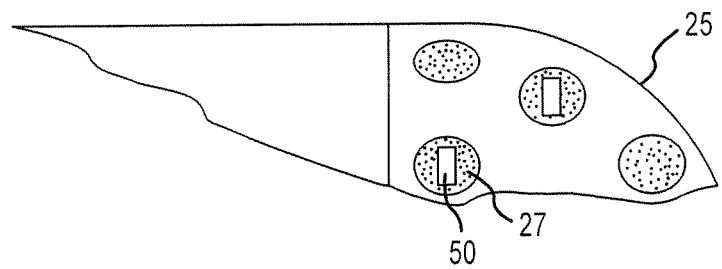
FIG. 4 is an close up view of certain features of the embodiment of FIG. 3.

In connection with FIGS. 3 and 4, a catheter according to other embodiments of the present invention will now be described. The embodiment depicted in FIGS. 3 and 4 is similar to the embodiment depicted in FIG. 1, and for brevity, the differences will be emphasized with the understanding that the description regarding FIG. 1 above also applies to the embodiment of FIGS. 3 and 4. The catheter 20 generally includes a proximal portion 22 and a catheter tip 25. Catheter tip 25 includes one or more holes 26 in which one or more sensors may be disposed. Holes 26 may have varying sizes, but if sized less than about 0.5 mm in diameter, there will be no appreciable impact on the lesion being formed by the catheter tip 25.

Anemometer 50 may be disposed in one of the holes 26 as further illustrated in FIG. 4. Preferably, anemometer is disposed and/or adhered in the hole using an insulative layer 27, such as a minimally-thermally-conductive adhesive. Preferably, insulative layer 27 is also non-electrically conductive. Anemometer 50 may be installed in one of the holes 26 and disposed to be flush with an exterior surface of catheter 20. When catheter 20 is used intravascularly, blood may flow across the tissue while catheter tip 25 is delivering ablation energy to the tissue. An anemometer 50 is disposed such that anemometer 50 can measure the cooling effect of the blood flowing over the tissue being treated.

In FIG. 3, anemometer 50 is positioned on the distal tip, but insulated from the conductive heat of the distal tip so that anemometer 50 may effectively measure the cooling effect of the surface perfusion. As discussed herein, anemometer 50 may be disposed in other locations on the distal portion of the catheter. Further, any number of anemometer circuits may be utilized as discussed above.

Figure 5:
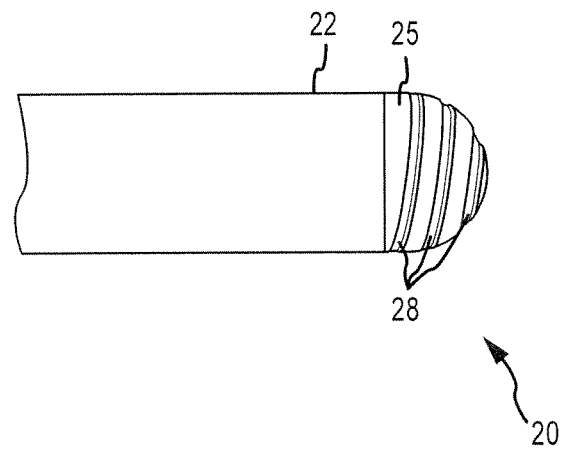
FIG. 5 is a side view of a catheter according to yet another embodiment of the present invention.
Figure 6:
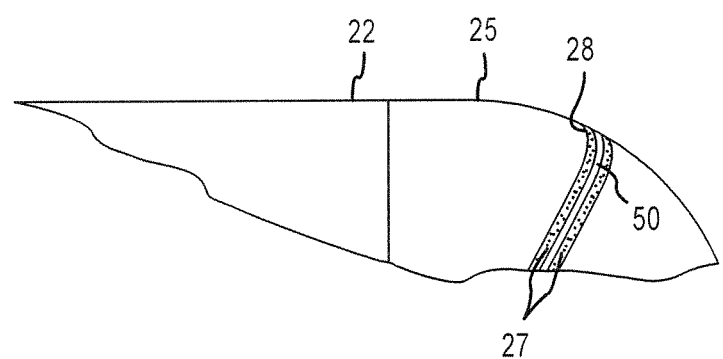
FIG. 6 is an close up view of certain features of the embodiment of FIG. 5.

In connection with FIGS. 5 and 6, a catheter according to other embodiments of the present invention will now be described. The embodiment depicted in FIGS. 5 and 6 is similar to the embodiment depicted in FIG. 1, and for brevity, the differences will be emphasized with the understanding that the description regarding FIG. 1 above also applies to the embodiment of FIGS. 5 and 6. The catheter 20 generally includes a proximal portion 22 and a catheter tip 25. Catheter tip 25 includes one or more grooves 28 in which one or more sensors may be disposed. For example, in FIG. 5, a single spiral groove is depicted, but additional grooves may be used. Anemometer 50 may be disposed in one of the grooves 28 as further illustrated in FIG. 6. Preferably, anemometer 50 is disposed and/or adhered in the hole using an insulative layer 27, such as a minimally-thermally-conductive adhesive. Preferably, insulative layer 27 is also non-electrically conductive. Groove 28 may have varying sizes, but if sized less than about 0.5 mm in width, there will be no appreciable impact on the lesion being formed by the catheter tip 25. Anemometer 50 may be installed in one of the grooves 26 and disposed to be flush with an exterior surface of catheter 20.

When creating lesions by ablation, it is desirable to know when to stop the application of ablation energy. The cooling effect created by fluid (e.g., blood) flowing over tissue complicates the ablation process. The flow of fluids (e.g., blood) during the ablation process is believed to significantly affect the time required to form lesions as well as affect the characteristics of the lesions being formed. Fluid flow can vary broadly based on location relative to pulmonary valves, or based on the extent of contractile motion (in sinus versus tachycardia).

A controller may be used with any of the catheter embodiments discussed above to help assist in the ablation process. The controller may include a lesion analysis processor to monitor all of the various system components to help determine when to stop the delivery of ablation energy. The processor may comprise a conventional general purpose computer, a special purpose computer, a distributed computer, or any other type of computer; the processor may comprise one or more processors, such as a single central-processing unit, or a plurality of processing units, commonly referred to as a parallel processing environment.

Figure 7:
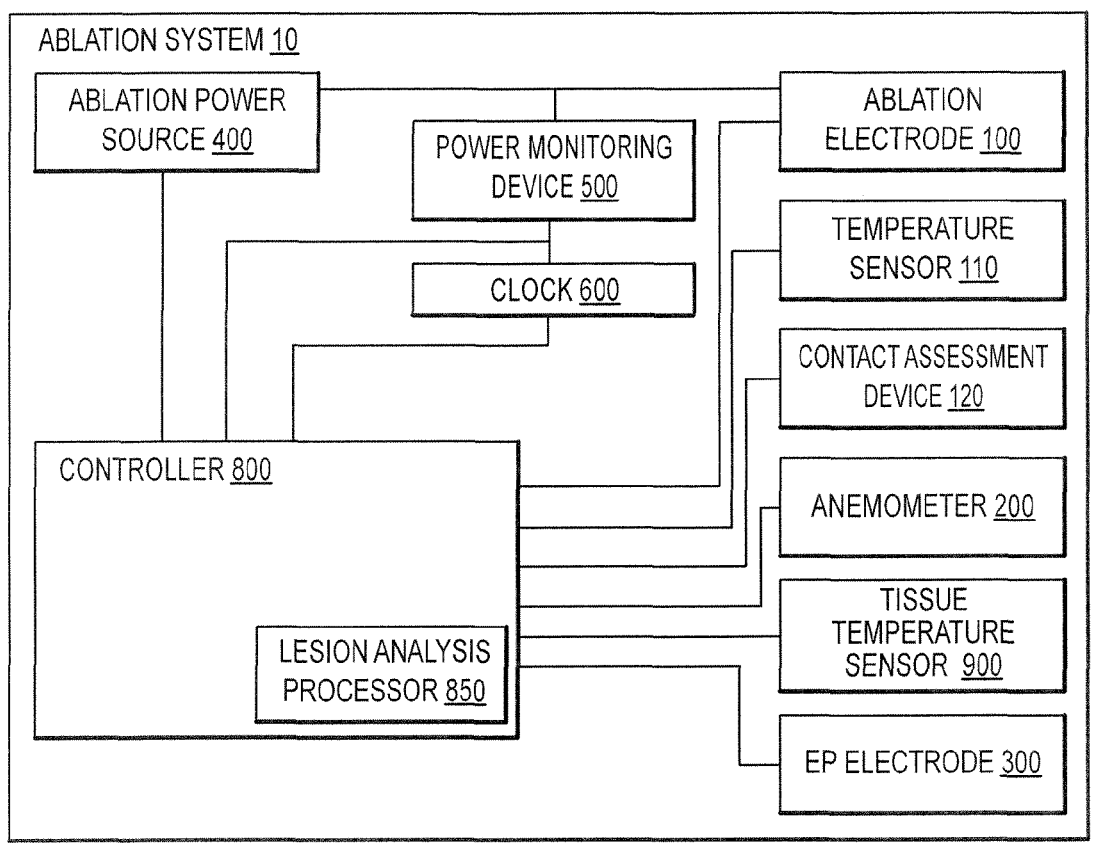
FIG. 7 is a block diagram representation of an ablation system in accordance with another embodiment of the present invention.

FIG. 7 is a block diagram of an ablation system 10 according to some embodiments of the present invention. The ablation system includes an ablation catheter, such as the ablation catheter described above. That is, the ablation system may include an ablation catheter having a proximal portion, a distal portion having a distal tip, at least one ablation electrode on the distal tip, a temperature sensor thermally coupled to the distal tip to measure the temperature of the distal tip, and an anemometer located on an exterior surface of the distal portion that is thermally isolated from the distal tip, thereby permitting the anemometer to measure the cooling effect of surface perfusion. The anemometer may be placed within a groove or a hole on the distal tip of the ablation catheter. At least one ablation electrode, temperature sensor, and anemometer are represented in FIG. 7 as blocks 100, 110, and 200, respectively.

A power source 400 is coupled to at least one ablation electrode 100. Power source 400 may be programmable to deliver at least one programmable level of power to at least one ablation electrode 100.

The ablation system also includes a contact assessment device 120. Contact assessment device 120 assesses a degree of contact between the ablation catheter and tissue being treated. In some embodiments of the invention, contact assessment device 120 is a force sensor located on the distal portion of the ablation catheter.

It is also contemplated that temperature sensor 110 may serve as contact assessment device 120, for example by monitoring for a change in temperature indicative of contact with the tissue to be treated.

In still other embodiments, contact assessment device 120 may include temperature sensor 110, ablation electrode 100, and power source 400. In these embodiments of the invention, power source 400 may supply a low level of power to ablation electrode 100 that is sufficient to cause a measurable increase in temperature of any tissue in contact with the ablation device without being sufficient to actually ablate the tissue. Temperature sensor 110 may monitor for this increase as an indication that ablation electrode 100 is in contact with tissue.

The ablation system also generally includes a power monitoring device 500 that is configured to monitor the amount of ablation power that is delivered by the ablation catheter (e.g., by ablation element 100), a clock 600 that is configured to measure a time period during which ablative power is delivered to the tissue being treated, and a lesion analysis processor 850 that is configured to estimate lesion formation. In estimating lesion formation, lesion analysis processor 850 may make use of: (1) an output of anemometer 200 that provides information on surface perfusion; (2) an output of contact assessment device 120 (e.g., a force sensor output); (3) an output of clock 600; (4) an output of power monitoring device 500; (5) tissue thickness; (6) internal perfusion; and (7) any combinations thereof. The processor may comprise a conventional general purpose computer, a special purpose computer, a distributed computer, or any other type of computer; the processor may comprise one or more processors, such as a single central-processing unit, or a plurality of processing units, commonly referred to as a parallel processing environment.

The ablation system may also include a controller 800 coupled to power source 400 and lesion analysis processor 850 such that controller 800 can regulate power source 400 based on information provided by lesion analysis processor 850. Generally speaking, controller 800 estimates size and/or quality of the lesion being formed and controls power source 400 accordingly. For example, controller 800 may deactivate power source 400 when the estimated lesion size exceeds a target size. Additional methods of controller power source 400 are discussed in detail below. The controller may comprise hardware and/or software, and may utilize a conventional general purpose computer, a special purpose computer, a distributed computer, or any other type of computer; the controller may comprise one or more processors, such as a single central-processing unit, or a plurality of processing units, commonly referred to as a parallel processing environment.

While processor 850 is depicted as being part of the controller 800, one of ordinary skill will appreciate that processor 850 may be configured to operate independently of controller 800, provided they are capable of sharing at least some information.

In some embodiments of the invention, the ablation system includes at least one tissue temperature measurement device 900 coupled to controller 800. This permits controller 800 to regulate power source 400 based upon tissue temperature. For example, controller 800 may deactivate power source 400 if the measured temperature of the tissue being ablated exceeds a maximum desirable temperature. Tissue temperature measurement device 900 may be a thermistor, a thermocouple, a second anemometer located on an exterior surface of the distal portion of the ablation catheter, or any other suitable temperature measurement device. It is also contemplated that temperature sensor 110 may be used to measure both the temperature of the distal tip of the ablation catheter and the temperature of adjacent tissue being ablated.

An electrophysiology electrode 300 may also be part of the ablation system. For example, the distal portion of the ablation catheter may carry one or more electrophysiology electrodes to measure electrical activity associated with tissue to be treated. The electrophysiology electrode(s) may be coupled to controller 800 to allow controller 800 to monitor for a change in an output of the electrophysiology electrode that is indicative of the tissue having been sufficiently ablated to create a conduction block.

Although at least four embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An ablation catheter for ablating tissue in need of treatment, wherein the tissue is subjected to surface perfusion, comprising:
   a proximal portion and a distal portion, said distal portion having a distal tip;
   at least one ablation electrode on the distal tip; and
   an anemometer located on an exterior surface of the distal portion, said anemometer being thermally isolated from the distal tip to permit the anemometer to measure a cooling effect of surface perfusion, and wherein the anemometer comprises a bridge circuit having at least one hot wire located on the surface of the distal portion and at least one resistor of the bridge circuit located within the ablation catheter.

2. The ablation catheter of claim 1 wherein the anemometer is located on the distal tip, the ablation catheter further comprising thermal insulation to insulate the anemometer from the distal tip.

3. The ablation catheter of claim 1 wherein the anemometer is located proximal of the distal tip.

4. The ablation catheter of claim 1 wherein the distal tip includes one or more spiral grooves, and the anemometer is positioned within a spiral groove.

5. The ablation catheter of claim 4 further comprising thermal insulation between the anemometer and the spiral groove.

6. The ablation catheter of claim 5 wherein the spiral groove is less than about 0.5 mm wide.

7. The ablation catheter of claim 1 wherein the distal tip has one or more holes of less than about 0.5 mm in diameter, and wherein the anemometer is positioned within one or more holes.

8. The ablation catheter of claim 7 further comprising thermal insulation between the anemometer and the distal tip.

9. The ablation catheter of claim 1 wherein the anemometer is located proximally of the distal tip and comprises a film circuit having the bridge circuit with at least one temperature responsive resistor encased with a thermally-conductive, electrically insulative material.

10. The ablation catheter of claim 1 further comprising a contact sensor on the distal portion that assesses a degree of contact between the ablation catheter and tissue being treated.

11. An ablation system for ablating tissue in need of treatment, comprising:
    an ablation catheter having:
       a proximal portion and a distal portion, said distal portion having a distal tip;
       at least one ablation electrode on the distal tip; and
       an anemometer located on an exterior surface of the distal portion, said anemometer being thermally isolated from the distal tip to permit the anemometer to measure a cooling effect of surface perfusion and wherein the anemometer comprises a bridge circuit having at least one hot wire located on the surface of the distal portion and at least one resistor of the bridge circuit located within the ablation catheter;
    a contact assessment device that assesses a degree of contact between the ablation catheter and tissue being treated;
    a power source coupled to the at least one ablation electrode, said power source being programmable to deliver at least one programmable level of power;
    a clock to measure a time period during which ablative power is delivered to the tissue being treated;
    a power monitoring device to monitor the amount of ablation power that is delivered by the ablation catheter; and
    a lesion analysis processor for estimating lesion formation as a function of at least: i) an output of the anemometer that provides information on surface perfusion; ii) an output of the contact assessment device; iii) an output of the clock; and iv) an output of the power monitoring device.

12. The ablation system of claim 11 wherein the contact assessment device is a force sensor located on the distal portion of the ablation catheter that assesses a degree of contact between the ablation catheter and tissue being treated.

13. The ablation system of claim 11 wherein the contact assessment device comprises a temperature sensor thermally coupled to the distal tip, which temperature sensor monitors for a change in temperature indicative of contact with the tissue to be treated.

14. The ablation system of claim 11 wherein the contact assessment device comprises a temperature sensor thermally coupled to the distal tip, the ablation electrode, and the power source, wherein the ablation system applies a low level of power sufficient to cause a measurable increase in a temperature of any tissue in contact with the ablation electrode, but insufficient to ablate the tissue, and the temperature sensor monitors for a change in temperature indicative of tissue being in contact with the ablation electrode.

15. The ablation system of claim 11 further comprising a controller coupled to the power source and to the lesion analysis processor, said controller regulating the power source based on information provided by the lesion analysis processor.

16. The ablation system of claim 15 further comprising at least one tissue temperature measurement device coupled to the controller such that if the temperature of the tissue being ablated exceeds a maximum desirable temperature, the controller will deactivate the power source.

17. The ablation system of claim 16 wherein the at least one tissue temperature measurement device comprises a thermistor.

18. The ablation system of claim 16 wherein the at least one tissue temperature measurement device comprises a second anemometer located on an exterior surface of the distal portion, said second anemometer being located in a position such that it can measure a temperature of the tissue being treated.

19. The ablation system of claim 15 further comprising:
an electrophysiology electrode located on the distal portion to measure electrical activity associated with tissue to be treated;
wherein the controller is coupled to the electrophysiology electrode and monitors for a change in an output of the electrophysiology electrode that is indicative of the tissue having been sufficiently ablated to create a conduction block.

20. The ablation system of claim 15 wherein the controller estimates a size of the lesion being formed during treatment and deactivates the power source when the estimated lesion size exceeds a target size.

21. The ablation system of claim 11 wherein the lesion analysis processor further estimates lesion formation as a function of: v) tissue thickness; and vi) internal perfusion.

22. The ablation system of claim 11 wherein the distal tip includes one or more grooves, and the anemometer is positioned within one of the grooves.

23. The ablation system of claim 11 wherein the distal tip includes one or more holes less than about 0.5 mm in diameter, and the anemometer is positioned within one of the holes.

24. A method of ablating tissue comprising:
placing an ablation catheter in contact with tissue to be ablated, said catheter having:
a proximal portion and a distal portion, said distal portion having a distal tip;
an ablation electrode located in the distal tip coupled to an ablation energy source for delivering ablation energy to the tissue; and and
an anemometer located on an exterior surface of the distal portion, said anemometer is positioned to permit the anemometer to measure a cooling effect of surface perfusion and wherein the anemometer comprises a bridge circuit having at least one hot wire located on the surface of the distal portion and at least one resistor of the bridge circuit located within the ablation catheter;
activating the ablation energy source to deliver ablation energy to the tissue to be ablated;
using an output of the anemometer to estimate lesion formation; and
deactivating the ablation energy source when an estimated lesion formation reaches a desired level.

25. The method of claim 24 further comprising:
assessing a degree of contact between the catheter and tissue being treated; and
measuring the amount of ablation energy that is delivered to the tissue being treated as a function of time;
wherein using an output of the anemometer to estimate lesion formation comprises:
using a processor to estimate lesion formation as a function of at least: i) an output of the anemometer that indicates an amount of surface perfusion; ii) the assessed degree of contact; and iii) the measured amount of ablation energy that is delivered over a treatment period of time.

26. The method of claim 24 further comprising monitoring a temperature of the tissue being treated and deactivating the ablation energy source if the monitored tissue temperature exceeds a maximum desired tissue temperature.

27. The method of claim 24 further comprising using the anemometer to estimate a velocity of a fluid passing over the anemometer.

\* \* \* \* \*